United States Patent
Moeck

(10) Patent No.: US 8,131,481 B2
(45) Date of Patent: Mar. 6, 2012

(54) DATABASE SUPPORTED NANOCRYSTAL STRUCTURE IDENTIFICATION BY LATTICE-FRINGE FINGERPRINTING WITH STRUCTURE FACTOR EXTRACTION

(75) Inventor: Peter Moeck, Portland, OR (US)

(73) Assignee: State of Oregon acting by and through the State Board of Higher Education on behalf of Portland State University, Portland, OR (US)

(*) Notice: Subject to any disclaimer, the term of this patent is extended or adjusted under 35 U.S.C. 154(b) by 794 days.

(21) Appl. No.: 11/800,422

(22) Filed: May 3, 2007

(65) Prior Publication Data
US 2008/0275655 A1  Nov. 6, 2008

(51) Int. Cl.
*G01N 31/00* (2006.01)
(52) U.S. Cl. .................................................. 702/27
(58) Field of Classification Search ........... 702/27, 702/28
See application file for complete search history.

(56) References Cited

U.S. PATENT DOCUMENTS

| | | | |
|---|---|---|---|
| 4,553,030 | A | 11/1985 | Tokiwai et al. |
| 5,168,457 | A | 12/1992 | Karen et al. |
| 5,235,523 | A | 8/1993 | Karen et al. |
| 6,732,054 | B2 | 5/2004 | Hart |
| 2002/0183861 | A1* | 12/2002 | McRee et al. ............ 700/1 |
| 2003/0198997 | A1* | 10/2003 | Von Dreele ............ 435/7.1 |

FOREIGN PATENT DOCUMENTS
JP  06-074967  4/1994

OTHER PUBLICATIONS

Bendersky et al., "Electron Diffraction Using Transmission Electron Microscopy," J. Research of the National Inst. of Standards and Technology 106:997-1012 (2001).
Berman "The Protein Data Bank: A Historical Perspective," Acta Cryst. A64: 88-95 (Jan. 2008).
Bigelow, et al., "Two New Indexes to the Powder Diffraction File," in *Electron Microscopy, Diffraction, and Microprobe Analysis*, ASTM publications, pp. 54-89 (1965).
Billinge et al., "The Problem with Determining Atomic Structure at the Nanoscale," Science 316: 561-565 (Apr. 27, 2007).
Biskupek et al., "Practical considerations on the determination of the Accuracy of the Lattice Parameter Measurements from Digital Recorded Diffractograms," J. Electron. Microsc. 53:601-610 (2004).
Blackman "On the Intensities of Electron Diffraction Rings," Proceedings of the Royal Society of London, Series A, Math and Physical Sciences 173:68-82 (1939).

(Continued)

*Primary Examiner* — Drew A Dunn
*Assistant Examiner* — Stephen Cherry
(74) *Attorney, Agent, or Firm* — Klarquist Sparkman, LLP

(57) ABSTRACT

Candidate structures for nanocrystal and other specimens are obtained based on a specimen complex spectrum that is determined as a Fourier transform of a phase-contrast electron micrograph. The specimen can also be assessed based on an amplitude portion of the complex spectrum using a lattice-fringe fingerprint. In some examples, the specimen complex spectrum is compensated based on an electron microscope transfer function, a specimen tilt, or based on other crystallographic compensation. Amplitude or phase portions of the compensated complex spectrum can be compared with reference structures stored in one or more reference structure databases.

14 Claims, 6 Drawing Sheets

OTHER PUBLICATIONS

Carr et al., "A Search/Match Procedure for Electron Diffraction Data Based on Pattern Matching in Binary Bit Maps," Powder Diffraction 1:226-234 (1986).
Carr et al., "Identification of Unknowns in Electron Diffraction," Electron Diffraction Techniques 1:212-215 (1992).
Carr et al., "NIST/Sandia/ICDD Electron Diffraction Database: A Database for Phase Identification by Electron Diffraction," J. Res. Natl. Inst. Stds. Technol. 94:15-20 (1989).
Clegg, Crystal Structure Determination. Oxford University Press (2005).
de Rosier et al., "Reconstruction of Three Dimensional Structures from Electron Micrographs," Nature 217:130-134 (Jan. 1968).
de Ruijter, "Measurement of Lattice-Fringe Vectors from Digital HREM Images: Theory and Simulations," J. Comp. Assist. Microsc. 6:195-212 (1994).
de Ruijter et al., "Measurement of Lattice-Fringe Vectors from Digital HREM iMages: Experimental pRecision," Ultramicroscopy 57:409-422 (1995).
de Ruijter et al., "Quantification of High-Resolution Lattice Images and Electron Holograms," Scanning Microscopy Supplement 6:347-359 (1992).
Dorset, "Electron Crystallography," Acta Cryst. B52: 753-769 (1996).
Erickson et. al., "Measurement and Compensation of Defocusing and Aberrations by Fourier Processing of Electron Micrographs," Phil. Trans. Roy. Soc. Lond. B. 261:105-118 (1971).
Faber, "ICDD's New PDF-4 Organic Database: Search Indexes, Full Pattern Analysis and Data Mining," Crystallography Reviews 10:97-107 (2004).
Fraundorf et al., "Making Sense of Nanocrystal Lattice Fringes," J. Appl. Phys. 98:114308-1-114308-10 (2005).
Hanawalt et al., "Identification of Crystalline Materials: Classification and Use of X-ray Diffraction Patterns," Ind. Eng. Chem. Anal. 8:244-247 (1936).
Hart, "ZONES: A Search/Match Database for Single-Crystal Electron Diffraction," J. Appl. Cryst 35:552-555 (2002).
Hovmöller et al. "Crystal Structure Determination from EM Images and Electron Diffraction Patterns," in Advances in Imaging and Electron Physics: Microscopy, Spectroscopy, Holography and Crystallography with Electrons, vol. 123, Academic Press, Peter W. Hawkes, pp. 257-289 (2002).
International Union of Crystallography, "CIF Frequently Asked Questions," available on the Intranet at http://www.iucr.org/iucr-top/cif/faq/ accessed Oct. 29, 2007.
Humphreys, "The Scattering of Fast Electrons by Crystals," Rep. Prog. Phys. 42:1826-1887 (1979).
Klug et al., "Optical filtering of Electron Micrographs: Reconstruction of One-Sided Images," Nature 212:29-32 (Oct. 1966).
Lyman et al., "Identification of Unknowns," Electron Diffraction Techniques 2:373-417 (1992).
Mighell et al., "A New Method for Phase Identification for Electron Diffractionists," J. Electr. Microsc. Techn. 16:155-159 (1990).
Moeck, "Crystallographic Databases: Past, Present, and Development Trends," Materials Science and Technology: Fundamentals and Characterization 1:529-540 (Oct. 2006).
Moeck "Structural Identification of Nanocrystals in the Transmission Electron Microscope," Proceedings of the Annual Meeting of the Minerals, Metals, and Materials Society (Mar. 2008).
Moeck et al., "Freely Accessible Crystallographic Internet Resources for Materials Science Education and Research," Materials Science and Technology: Fundamentals and Characterization 1:119-128 (Oct. 2006).
Moeck et al., "Fringe Fingerprinting and Transmission Electron Goniometry, supporting Image-based Nanocrystallography in Two and Three Dimensions," Proc. $9^{th}$ World Multi-Conference on Systemics, Cybernetics and Informatics, Orlando, Florida (Jul. 10-13, 2005).
Moeck et al., "Identifying Unknown Nanocrystals by Fringe Fingerprinting in Two Dimensions & Free-Access Crystallographic Databases," Two- and Three-Dimensional Methods for Inspection and Metrology III, edited by K.G. Harding, Proc. of SPIE 6000:60000M-1-60000M-12 (2005).
Moeck et al., "Image-Based Nanocrystallography with On-Line Database Support," Proc. of SPIE 6370:63701A (Oct. 2006).
Moeck et al., "Lattice-Fringe Fingerprinting of an Iron-Oxide Nanocrystal Supported by an Open-Access Database," Proc. NSTI-Nanotech 4:93-96 (May 20, 2007).
Moeck et al., "Lattice-Fringe Fingerprinting: Structural Identification of Nanocrystals by HRTEM," in Quantitative Electron Microscopy for Materials Science, edited by E. Snoeck, R. Dunin-Borkowski, J. Verbeeck, and U. Dahmen (Mater. Res. Soc. Symp. Proc. 1026E, Warrendale, PA, Nov. 2007).
Moeck et al., "Structural Fingerprinting in the Transmission Electron Microscope: Overview and Opportunities to Implement Enhanced Strategies for Nanocrystal Identification," Z. Kristallogr. 222:634-645 (Nov. 2007).
Nicolopoulos et al., "New Instrumentation for TEM Electron Diffraction Structure Analysis: Electron Diffractometry Combined with Beam Precession," in Electron Crystallography: Novel Approaches for Structure Determination of Nanosized Materials, Ed. by Thomas Weirich, et al., Springer Netherlands, pp. 169-183 (Feb. 2006).
Own et al., "Prospects for Aberration Corrected Electron Precession," Ultramicroscopy 107:534-542 (Jun.-Jul. 2007).
Rhodes, Crystallography Made Crystal Clear, Third Edition, Academic Press (Feb. 2006).
Stadelmann, JEMS, A Software Package for Electron-Diffraction Analysis and HREM Image Simulation, CIME-EPFL. (2004) http://cimewww.epfl.ch/people/stadelmann/jemsWebSite/jems.html.
Spence et al., "Automated Electron Nanocrystallography," Mater. Res. Soc. Symp. Proc. 1026: 1026-C19-01 (Nov. 2007).
Villars et al., "Interplay of Large Materials Databases, Semi-Empirical Methods, neuro-Computing and First Principle Calculations for Ternary Compound Former-Norformer Prediction," Engineering Applications of Artificial Intelligence 13:497-505 (2000).
Woolfson, "X-Ray Crystallography," Nature 193:104-105 (Jan. 1962).
Zou et al., "Electron Crystallography: Imaging and Single-Crystal Diffraction from Powders," Acta Cryst. A64:149-160 (Jan. 2008).
Zuo et al., "Electron Crystallography: Structure Determination by HEM and Electron Diffraction," in Industrial Applications of Electron Microscopy, Zhigang Li ed., CRC, pp. 583-614 (2002).

* cited by examiner

US 8,131,481 B2

DATABASE SUPPORTED NANOCRYSTAL STRUCTURE IDENTIFICATION BY LATTICE-FRINGE FINGERPRINTING WITH STRUCTURE FACTOR EXTRACTION

ACKNOWLEDGMENT OF GOVERNMENT SUPPORT

This invention was made with government support under Grant Number N00014-07-1-0457 awarded by the Office of Naval Research. The government has certain rights in the invention.

FIELD

The present application is directed to methods of crystallographic structure identification.

BACKGROUND

For nanomaterials made of crystals of dimensions on the order of a few nanometers, material properties frequently depend on crystal size. For nanocrystals, there is a tendency to metastability that is dependent on nanocrystal processing conditions. Nanocrystals of the same stoichiometry and size may exhibit different crystal structures. Because nanocrystal structure partially determines nanomaterial properties, methods that provide information on crystal structures are important for the effective use and fabrication of nanomaterials.

One conventional method of structure identification is based on powder X-ray diffraction. In powder X-ray diffraction fingerprinting, three-dimensional (3D) crystal structure information is collapsed into a one-dimensional intensity profile as a function of scattering angle or reciprocal lattice vector. Bragg diffraction peaks in such diffractograms provide fingerprint information. Unfortunately, powder X-ray methods are of limited usefulness for identifying crystal structures in the nanometer size range. In addition, some technologically important nanomaterials such as, e.g., vanadium-oxide nanotubes, do not produce characteristic powder X-ray diffraction fingerprints. Thus improved identification methods for nanocrystals are needed.

SUMMARY

Representative methods comprise determining a complex spectrum associated with a specimen based on a specimen micrograph and comparing structure factor fingerprint information associated with at least one candidate structure with corresponding specimen structure factor fingerprint information based on the complex spectrum. Based on the comparison, a determination is made if the specimen structure corresponds to the at least one candidate structure. In some examples, the structure factor fingerprint information is based on at least one phase of the complex spectrum. In some examples, the complex spectrum is a crystallographically compensated complex spectrum. In additional examples, at least one candidate structure is identified from a set of one or more predetermined reference structures based on a comparison of specimen lattice-fringe fingerprint information with lattice-fringe fingerprint information associated with the one or more predetermined reference structures. In further examples, the at least one candidate structure is selected from a set of one or more predetermined reference structures based on a comparison of specimen chemical fingerprint information with chemical fingerprint information associated with the one or more predetermined reference structures. In some examples, lattice-fringe fingerprint information for at least one reference structure is obtained based on reference data stored in at least one database. In other examples, lattice-fringe fingerprint information for the specimen is added to the at least one database. In further representative examples, a specimen structure is assessed to determine whether the structure corresponds to at least one of the reference structures based on figures of merit assigned to each of the candidate structures. In representative examples, the micrograph is a phase-contrast transmission electron micrograph.

A representative embodiment includes computer readable media containing computer-executable instructions for a method that comprises determining a complex spectrum associated with a specimen based on a specimen micrograph. Structure factor fingerprint information associated with at least one reference structure is compared with corresponding specimen structure factor fingerprint information based on the complex spectrum. Based on the comparison, a determination is made as to whether the specimen structure corresponds to the at least one reference structure. In further examples, the complex spectrum is processed to obtain a crystallographically compensated complex spectrum.

Another representative embodiment includes an apparatus comprising an electron microscope configured to produce a phase-contrast specimen micrograph. A processor is configured to produce a complex spectrum from a numerical image representation obtained from the micrograph. Based on at least a phase portion of the complex spectrum, a specimen structure is compared with at least one reference structure. In other examples, the apparatus comprises a display configured to display an identification of at least one candidate structure based on the comparison. In further representative examples, the processor is coupled to at least one reference structure database and is configured to compare a specimen structure with the at least one reference structure based on reference structure data received from the reference structure database. In some examples, the specimen structure is compared with the at least one reference structure based on an amplitude portion of the complex spectrum. In alternative examples, the amplitude portion comparison is based on at least one lattice-fringe fingerprint of the at least one reference structure. In some alternatives, a plurality of candidate structures is selected from the reference structures. In additional examples, the processor is configured to indicate that the database does not include a reference structure corresponding to the specimen structure. In further examples, the processor is configured to produce specimen reference data based on a reference structure format associated with the at least one database. In other examples, the processor is configured to direct the reference specimen data to the at least one database or to assess each of a plurality of reference structures based on a reference structure database and assign a figure of merit to each.

The foregoing and other objects, features, and advantages of the disclosed technology will become more apparent from the following detailed description, which proceeds with reference to the accompanying drawings.

DETAILED DESCRIPTION

As used in this application and in the claims, the singular forms "a," "an," and "the" include the plural forms unless the context clearly dictates otherwise. Additionally, the term "includes" means "comprises." Further, the term "coupled" means electrically, electromagnetically, mechanically, or optically coupled or linked and does not exclude the presence of intermediate elements between the coupled items.

The described systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Figure 1:
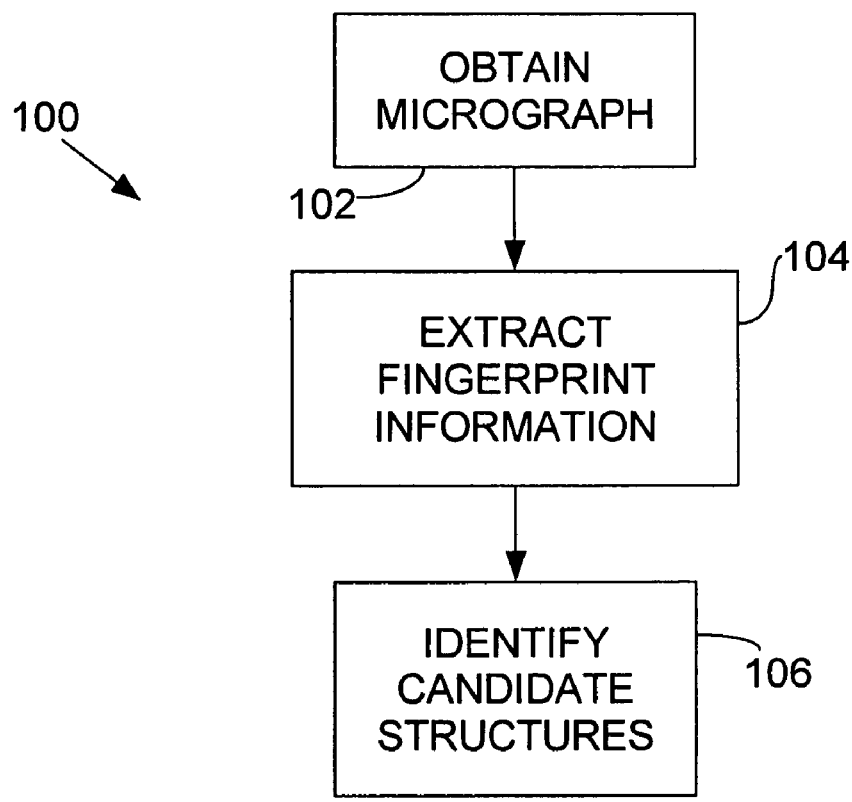
FIG. 1 is a simplified block diagram of a representative structural fingerprinting method.

A representative fingerprinting method 100 is illustrated in FIG. 1. As noted above, such structural fingerprinting methods are typically intended for the identification or classification of an unknown specimen structure based on experimentally obtained information about the specimen. In a step 102, a micrograph of a specimen is obtained. The micrograph is typically an image of the specimen taken with an appropriate imaging apparatus such as, an electron microscope. In some examples, the specimen includes at least one nanocrystal situated so that the micrograph exhibits at least one non-parallel set of lattice-fringes. While the micrograph can be displayed as, for example, a two-dimensional image, the micrograph is generally associated with a numerical image representation that consists of intensity as a function of position. The micrograph is conveniently associated with a two dimensional (2D) image, but a series of one dimensional images or a three dimensional image such as a "data cube" can also be used. Typically, useful three dimensional images contain a series of 2D images recorded at different focal settings or a 2D image combined with spectroscopic information.

In a step 104, fingerprint information about the specimen is obtained from the micrograph. Fingerprint information is, in general, information about a specimen that is characteristic of the specimen and that may be used to distinguish the specimen from other specimens or groups of specimens. If the fingerprint information obtained in the step 104 is sufficiently characteristic, the specimen may be identified as corresponding to a single candidate structure. However, in many examples, complete structural identification is not obtained, but a number of likely candidate structures are determined in a step 106.

Although a micrograph of a specimen can be obtained through various types of microscopes based on various forms of radiation (such as X-rays, other electromagnetic radiation, or charged or neutral particle beams), examples using electron micrographs are described herein. An electron micrograph is an image taken with an electron microscope such as a transmission electron microscope or other type of electron microscope. Such electron micrographs can provide information related to specimen topography, morphology, crystal structure, composition, or other specimen properties.

Electrons transmitted through the specimen can be detected to produce a transmission electron (TEM) micrograph. Some types of transmission electron microscopes include high-resolution TEM (HRTEM) and scanning TEM (STEM). Micrographs obtained with these or other instruments can be used in structural fingerprinting, but methods based on HRTEM micrographs are described herein as convenient examples.

A TEM can be used to capture an electron diffraction pattern as well as a specimen micrograph. These diffraction patterns typically consist of an arrangement of diffraction spots that indicate points of constructive interference of radiation diffracted by the specimen. The relative positions and arrangements of diffraction spots are indicative of the reciprocal lattice spacing for the specimen and therefore the unit cell of the real space crystal lattice of the specimen. Unfortunately, diffraction patterns contain structural information only in the form of the intensities of the diffraction spots, and thus provide only incomplete information about the atomic arrangement within the unit cell of the crystal lattice. This incomplete information is associated with the so-called "phase problem." However, such incomplete information about a specimen can be used to select possible candidate structures for the specimen. Such a selection process does not always identify a specimen structure, but limits subsequent evaluation based on more complete specimen information to a number of candidate structures.

Figure 2:
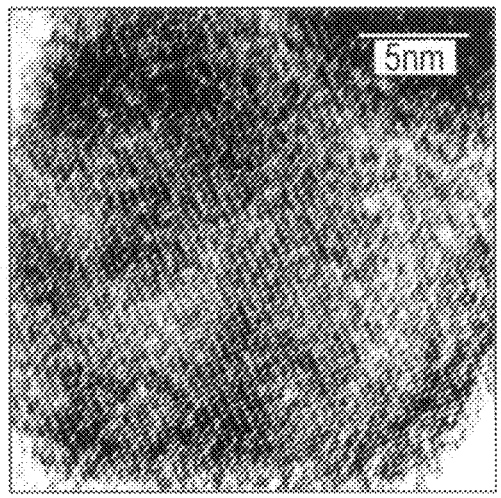
FIG. 2 is a high-resolution phase-contrast transmission electron micrograph of an iron-oxide nanocrystal specimen that includes a mixture of magnetite and maghemite nanocrystals.

TEMs can be operated in a phase-contrast mode to capture lattice-fringe patterns. A representative phase-contrast micrograph of a nanocrystal sample obtained by HRTEM is shown in FIG. 2. Such phase-contrast images are typically captured with a defocused electron microscope, and often with the microscope at a so-called Scherzer focus. Images captured at the Scherzer focus typically have directly interpretable contrast because of a relative balance of spherical aberration and defocus. In standard phase-contrast HRTEM, the point resolution is defined as the reciprocal value of the crossover of the contrast transfer function at the Scherzer focus of the microscope.

Periodic contrast variations in HRTEM, STEM, or other types of phase-contrast images are referred to herein as lattice fringes. In such images, fringe spacing is typically proportional to lattice spacing when the corresponding lattice planes meet the Bragg condition. These phase-contrast images provide information on both crystal structure and atomic coordinates, or a related electrostatic potential. Thus, phase-contrast images pose a potential solution to the diffraction pattern "phase problem."

The TEM electron beam exhibits a substantially stronger interaction with a sample than X-ray radiation used in conventional powder X-ray analysis. Thus in TEM, electrons can have a high probability of being multiply scattered as transmitted through the specimen, especially when a specimen is relatively thick. Geometrical structure or lattice spacing information can typically be reliably extracted, even in the case of thick specimens, from the relative arrangement of diffraction spots in the electron diffraction pattern. However, typically this information is inadequate for complete specimen characterization. For thick specimens exhibiting multiple scattering, dynamical diffraction theory can be used in specimen analysis to extract structure information from the diffraction spot intensities. However, the necessity of the application of dynamical diffraction theory and the associated thickness dependence can make reliable fingerprint information more difficult to obtain.

Single-crystal electron precession diffraction techniques permit the collection of diffraction patterns and diffraction spot intensities for thick crystals (up to several tens of nanometers thick) that can be reliably analyzed. These techniques operate in a so-called quasi-kinematic regime, where the application of the full dynamical scattering theory is no longer necessary. The electron precession method uses a precession of a parallel or focused electron beam around an optical axis rather than specimen movement around a fixed beam direction. The diffracted beams are de-scanned in such a manner that stationary diffraction patterns are obtained. Electron precession based diffraction patterns typically include more diffraction spots than conventional electron diffraction patterns. Thus, electron precession diffraction patterns are suitable for least-squares fits to larger systems of inhomogeneous linear equations and more accurate extraction of lattice parameters from diffraction spot arrangements. In addition, specimens do not need to be in an exact zone-axis orientation for lattice parameter extraction. Therefore, geometric structure information and diffraction spot intensities extracted from electron precession diffraction patterns can be useful for structural fingerprinting.

Although higher electron scattering efficiency can complicate the analysis of thick specimens (i.e., specimens having thicknesses associated with multiple scattering), such high scattering efficiency permits effective imaging of relatively thin samples that include one, a few, or many small crystals. For typical nanocrystal specimens, electrons can be assumed to experience a single scattering event without significant loss of accuracy and analysis can be based on a so-called kinematic scattering theory. More complex analysis based on dynamical scattering theory is unnecessary for such specimens. Thin samples (such as samples consisting of a few nanocrystals) can also be analyzed using a so-called weak-phase object approximation. In the weak-phase object approximation, the sample is assumed to cause systematic phase variations in the diffracted electron beam without introducing significant amplitude variations. For inorganic nanocrystal specimens that are thinner than about 10 nm, the kinematic approximation and the weak-phase object approximation are generally sufficient to complete specimen analysis.

When kinematic scattering theory and the weak-phase object approximation are appropriate, a phase-contrast electron micrograph of a specimen can be considered to directly constitute a projection of the electrostatic potential of the specimen. The phase variations imparted to the transmitted electron beam by the specimen are accurately represented by information that is related to the appearance of the lattice fringes in the electron micrograph image. Such a phase-contrast image can be used to estimate the projected electrostatic potential of the specimen which provides a detailed and highly characteristic specimen description that can be compared with standard reference data stored in a database and used for specimen identification or classification. Therefore, such images are useful for structural fingerprinting such as that shown in FIG. 1.

Micrograph Processing

Various processing techniques are typically performed on micrographs in order to extract fingerprint information. In typical examples, crystallographically compensated complex spectra (CCCSs) are obtained from a micrograph. In some examples, complex spectra are obtained from micrographs by a Fourier transform and Crystallographic Image Processing (CIP), though additional processing steps such as convolution with an aperture function or deconvolution with a microscope transfer function can be included. The CCCS is associated with the complex Fourier transform of the micrograph compensated for various influences of the microscope operating conditions and includes phase information that is lacking in conventional diffraction patterns. Generally, the CCCS is described as containing an amplitude portion and a phase portion. Structural fingerprinting information can be extracted from the CCCSs.

CIP is generally used for the correction of micrograph features associated with imperfect micrograph recording conditions. For instance, CIP can correct for the effects of electron beam tilt and crystal tilt, and for a particular phase-contrast transfer function of a microscope objective lens, including astigmatism and defocus. CIP is typically performed using a desktop computer with conventional processing software such as CRISP available from Calidris Software. Typically CRISP functions include quasioptical filtering, transfer function correction, and crystallographic symmetry averaging. While CIP and other compensation processing techniques are not necessary for structural fingerprinting in all cases, CIP typically increases the accuracy of extracted fingerprint information, particularly for specimens for which the weak-phase object and the kinematic diffraction limit approximations are appropriate.

Prior to the calculation of a complex spectrum (or a phase portion) associated with a specimen micrograph, a suitable area of a thin specimen is generally selected. Some amorphous support film or amorphous crystal margin region is typically included in this selection as well. In order to reduce adverse effects resulting from existing crystal tilt, the Fourier transform of the selected area is calculated under the constraint that its phase origin coincides with the crystallographically defined origin of one of the 17 plane or two-dimensional (2D) space groups.

An associated appropriate space group can be selected based on a process of origin refinement typically performed using CIP. Because the coefficients of the complex spectrum associated with the specimen exhibit symmetry associated with one of the 2D space groups, and each of these groups possesses a unique set of symmetry relations and restrictions for the possible phases of the complex spectrum, a space group or group of space groups can be selected based on the relative agreement or disagreement between the experimental complex spectrum and theoretical phase relations and restrictions for one or more of the space groups. A figure of merit can be defined that aids in the determination of the most probable crystal symmetry or symmetries. This procedure can involve testing all of the 17 plane space groups for many incrementally neighbouring positions within a projected unit cell in a specimen. A figure of merit can be used to identify a most probable subgroup of the 230 three-dimensional (3D) space groups, or a plurality of candidate subgroups.

Because the effects of the phase-contrast transfer function on the image can be compensated by CIP, image resolution need not be limited to the Scherzer (or point-to-point) resolution. This can be particularly important for TEMs with field emission electron sources in which image resolution can be much higher than the Scherzer resolution.

Structural fingerprint information extracted from a CCCS tends to be more reliable for specimens that exhibit low defect densities. Because only some $10^2$ to $10^3$ unit cells are generally needed for CIP, the structural fingerprinting methods disclosed herein are suitable for a wide variety of nanocrystal specimens.

Lattice-Fringe Fingerprint Information

As used herein, lattice fringes are periodic intensity variations that appear in phase-contrast specimen images (micrographs). A fringe is generally visible in a specimen image if its associated spatial frequency is reliably transferred to the image, i.e., the fringe spacing is larger than the point resolution of the microscope. Lattice plane spacings, lattice constants, and other geometrical-structural information can be obtained from fringe spacings and the angles of intersection of fringes in the micrograph. Such information can be referred to as lattice-fringe fingerprint information. The crystal structure of the sample can be identified, or a group of candidate structures can be selected, based on such fingerprint information.

Lattice-fringe fingerprint information is typically calculated from the Fourier transform of a micrograph of a specimen. Preferably, the crystallographically compensated complex spectrum is generated from the micrograph and the CCCS includes an amplitude portion and a complementary phase portion. The lattice-fringe fingerprint information can be based on the amplitude portion. When presented as a two-dimensional image, the amplitude portion includes a two-dimensional set of diffraction spots. A representative micrograph is illustrated in FIG. 2, and FIG. 3 is an example of an amplitude portion of a complex spectrum reduced to a plurality of diffraction spots.

Figure 3:
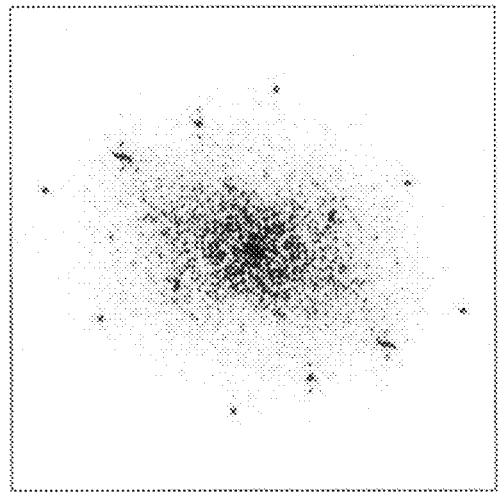
FIG. 3 is a Fourier transform amplitude spectrum based on the micrograph of FIG. 2.

The diffraction spots in FIG. 3 can be indexed with two-dimensional pseudo-Miller indices and the two shortest reciprocal lattice vectors that make an acute angle with each other are selected as the basis vectors of the 2D lattice of diffraction spots. The 2D lattice can be estimated by, for example, a least squares procedure that considers all diffraction spot locations and also the curvature of the Ewald sphere. This refinement can permit more accurate extraction of the lattice geometry from the spot arrangement in the amplitude spectrum. Based on the 2D lattice and the amplitude spectrum, the magnitudes of the reciprocal lattice vectors or other lattice-fringe fingerprint information can be obtained. Based on such analysis, the spectrum of FIG. 3 is shown as indexed with respect to a reciprocal lattice in FIG. 4.

Figure 5:
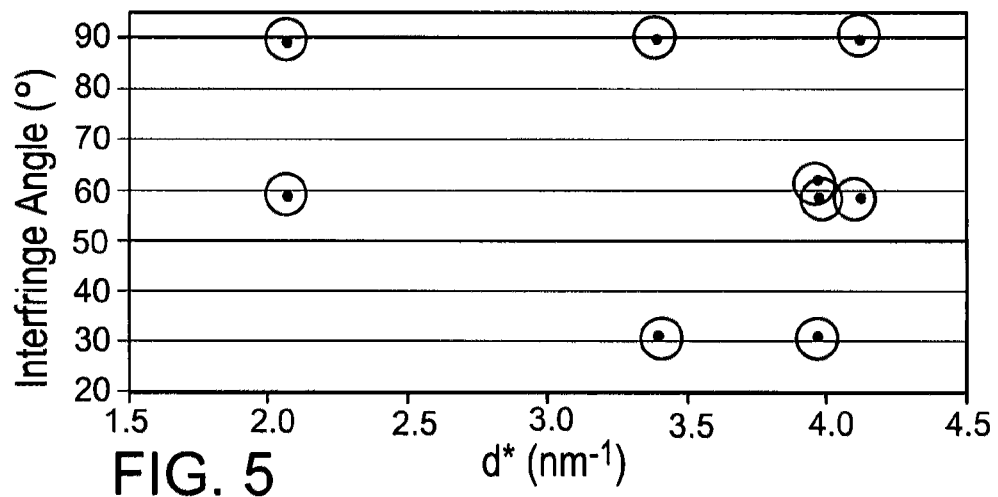
FIG. 5 is a lattice-fringe fingerprint plot based on the micrograph of FIG. 2.

Lattice-fringe information is typically presented in a fringe fingerprint plot such as the example fringe fingerprint plot of FIG. 5. Such plots show interfringe angles of crossed fringes as functions of respective reciprocal lattice spacings associated with the fringes. Fringe fingerprint plots contain more specimen identification information than typically obtained with conventional X-ray methods.

Fringe fingerprint plots also contain, in the kinematical limit, space group information such as the "signatures" of translation lattice types, glide planes, and screw axes in projection. Because all possible interfringe angles are the same for cubic crystals, space group information can be derived from fringe fingerprint plots. The crossing of two symmetrically related fringes results in one data point on a fringe fingerprint plot, while cross-fringes with different spacings result in two data points. For example, the presence or absence of data points in a fringe fingerprint plot of a cubic crystal is characteristic of its translation symmetry. Primitive space groups without screw axes and glide planes possess no systematic absences in fringe fingerprint plots.

The projected 2D symmetry of the sample can be used with either one of or both the amplitude and phase portions of the complex spectrum after CIP to provide additional information about the symmetry of the specimen structure. This is typically achieved by averaging the amplitudes and phases of the symmetry equivalent reflections or diffraction spots. In this manner, potential kinematically forbidden spots in the 2D lattice can be identified to be those that have intensities close to and including zero.

The identification of kinematically forbidden electron diffraction spots and the determination of space groups on the basis of spots from higher order Laue zones can also be based on electron diffraction patterns. Preferably, the electron diffraction pattern is obtained with electron precession techniques. This information can also be used for structural fingerprinting.

Figure 6:
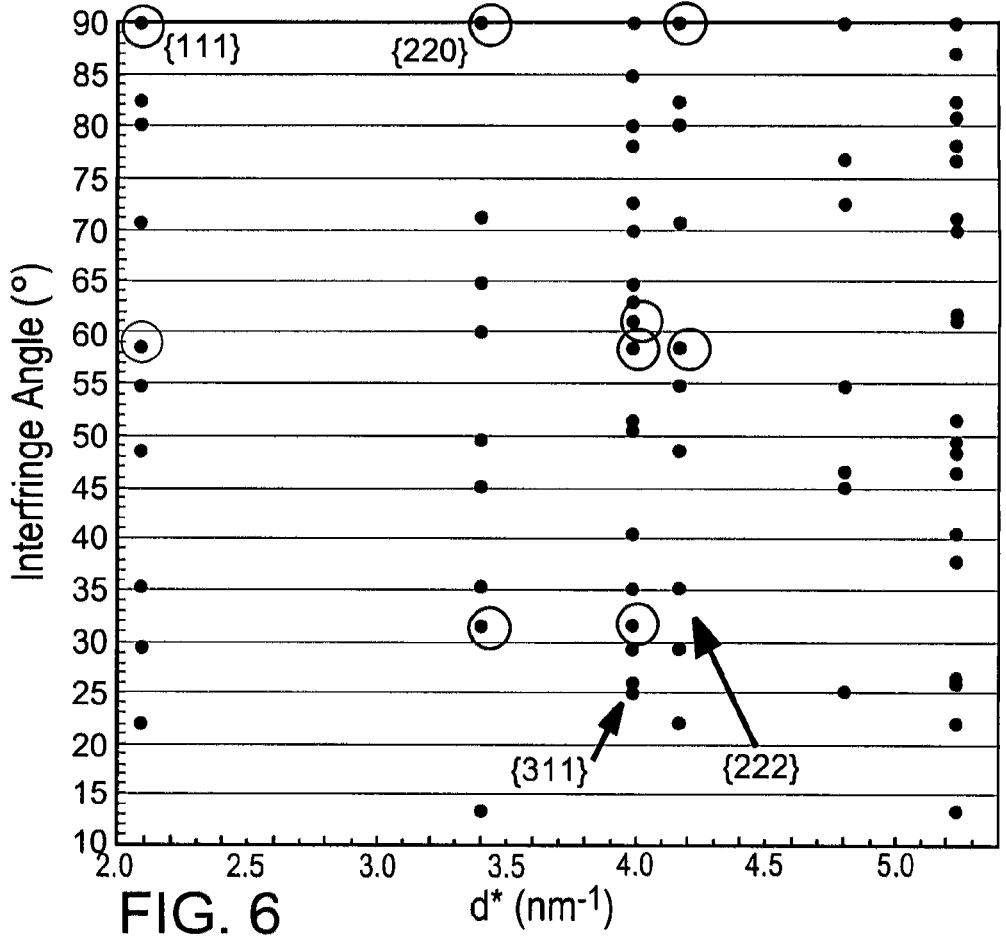
FIG. 6 is a theoretically generated lattice-fringe fingerprint plot for magnetite to which experimental values associated with the specimen micrograph of FIG. 2 have been added.

Structural fingerprinting can be based on a comparison of experimental lattice-fringe fingerprint plots with theoretically generated lattice-fringe fingerprint plots. Alternatively, a subset of candidate structures can be selected from a larger set of structures based on a comparison of the specimen lattice-fringe fingerprint plot and those of a group of known reference specimens. The specimen image includes at least two sets of non-parallel lattice fringes. An example of a theoretically generated lattice-fringe fingerprint plot is shown in FIG. 6. The circled dots indicate matches with the experimentally generated lattice-fringe fingerprint plot of FIG. 5.

More elaborate fringe fingerprint plots than those of FIGS. 5-6 can contain a histogram of the probability of observing crossed fringes in a specimen micrograph or the structure factor phase and/or amplitude in a third or higher dimension. Calculation of such probabilities for an ensemble of randomly oriented crystals is described in Fraundorf et al., "Making sense of nanocrystal lattice fringes," J. Appl. Phys. 98:114038 (2005) that is incorporated herein by reference. A tilt range over which any crossed-fringes are visible for a particular crystal thickness can also be determined. Typically, lattice fringes are visible over a larger range of angles when the specimen is a nanocrystal.

Another type of fringe fingerprint plot contains angular and spatial frequency ranges over which the fringe crossings or zone axes are visible. These ranges are functions of the crystal thicknesses. Fringe crossings are typically visible over a wider angular range for smaller crystals such as nanocrystals as can be calculated as described in the Fraundorf reference cited above. Fringe fingerprint plots can also include the structure factor amplitudes and phases.

Experimentally obtained fringe fingerprint plots tend to become more "characteristic" of a particular crystal with improved point resolution of the microscope. Therefore, higher-resolution images typically permit superior results.

While grain sizes of tens of nanometers to a few nanometers make powder X-ray diffraction challenging, such grain sizes simplify lattice-fringe fingerprinting. When crystal sizes are small, lattice fringes become visible over a wider angular range, and an increased number of data points is present in lattice-fringe fingerprint plots.

It is customary to record a so-called "through focus series" of HRTEM images above and mainly below the Scherzer focus with the corresponding objective aperture removed. Such focus changes modify the phase-contrast transfer function of the microscope objective lens in a predictable manner. Increasing underfocus, or imaging at a focus setting that is negative relative to the Scherzer focus, typically results in the visibility of higher spatial frequencies in HRTEM images. Increasing underfocus may, in this manner, effectively increase the resolution of the microscope. However, because the diffracted beams interfere with different objective-lens-induced phase shifts, the HRTEM image is not a directly interpretable structural image. Nevertheless, this behavior can be used for lattice-fringe fingerprinting (both in the weak phase object/kinematic diffraction limit and beyond) in order to confirm or reject a match to a candidate structure.

It is typically preferred that lattice-fringe fingerprinting identifications of unit cell geometries for nanocrystals be based on normalized reduced cells and perturbation stable cells. For the latter, possible distortions in the inter-axial angles of reduced unit cells are omitted in search/match procedures and all metrically similar lattices can be found.

Structure Factor Fingerprint Information

Estimates of the amplitudes and phases of the crystallographically defined structure factors can be extracted from the complex spectrum (or the crystallographically compensated complex spectrum). The structure factors represent the sums of waves that are diffracted from each of the atoms in a unit cell of the crystal lattice of the specimen. Interference of such waves produces an array of diffraction spots. Each diffraction spot is associated with at least an amplitude and a phase of a structure factor. For electron micrographs, each atom in the unit cells of a specimen diffracts the incident electron wave as a function of the local electrostatic potential. Structure factors and electrostatic potential are Fourier transform pairs. The complex structure factors (including both amplitude and phase) are characteristic of the atomic arrangement for any given structure and can facilitate the identification of an unknown crystal structure. Structure factor phases are typically more useful for structural fingerprinting than structure factor amplitudes because the phases tend to be relatively unaffected by crystal tilts. Crystal tilt can, on the other hand, significantly alter structure factor amplitudes, and the phase-contrast transfer function can attenuate these amplitudes in a nonlinear manner.

Within the kinematic scattering approximation, structure factors can be calculated directly from the crystallographically compensated complex spectrum. When the micrograph is a diffraction pattern, the structure factor amplitudes can be obtained from the intensity of the diffraction spots. For phase-contrast images, a complex spectrum can be obtained from the image and the complex structure factors can be calculated from the complex spectrum. Typically, structure factors are calculated from the crystallographically compensated complex spectra for superior results. The combined weak-phase object and kinematic diffraction approximations are frequently suitable for samples with grain sizes of tens of nm to a few nm. The crystal thickness limit up to which the specimen micrograph may be treated by the kinematic diffraction approximation varies from sample to sample and with the instrumental parameters. Factors that influence this limit are, for example, the weight of the constituent atoms, the crystal structure, and the acceleration voltage of the microscope. Complex structure factors that are calculated from such samples using the combined weak-phase object and kinematic diffraction approximations tend to produce reasonably accurate maps of the projected electrostatic potential. When the sample is a nanocrystal or a plurality of nanocrystals, the weak-phase object and kinematic diffraction approximations are generally sufficiently satisfied and the calculated projected electrostatic potential map, atomic coordinates, structure factor phases, complex structure factors, or the phase portion of the complex spectrum can be used for structural fingerprinting.

If specimen thickness exceeds the limit of the weak-phase object approximation, the pseudo-weak phase object approximation may be valid. It is known that HRTEM imaging within the pseudo-weak phase object is substantially equivalent to imaging a hypothetical isomorphic structure in which lighter atoms are replaced by heavier atoms and heavier atoms are replaced by lighter atoms. Atomic coordinates, however, remain the same so that the structure factor phases of the isomorphic equivalent are close to those of the real crystal structure.

Structure factor amplitudes can also be reliably extracted from the diffraction spot intensities of electron precession diffraction patterns because such techniques allow for the use of a quasi-kinematic approximation. Electron precession diffraction techniques can be useful for analyzing specimens with thicknesses on the order of 20 nm, because the processed diffraction patterns will fulfill the kinematic approximation reasonable well. Structure factor amplitudes obtained in this manner can be useful for structural fingerprinting.

Databases

The structural fingerprinting of an unknown specimen can be accomplished through a comparison of fingerprint information obtained from the unknown structure with corresponding information for one or more reference structures. Descriptions of these reference structures can be contained in one or more databases and all the structures in the database may be searched for selection of likely candidate structures. Databases for structural fingerprinting generally contain fingerprint information for all reference structures or other information from which the fingerprint information can be calculated. If, for example, complex structure factor fingerprint information is used for identification, then a preferred database contains complex structure factors of reference structures. Alternatively the database can contain any information sufficient to calculate the structure factors. For example, the database can contain parameters related to the atomic coordinates and information about the scattering process such as the atomic scattering factors as a function of experimental parameters.

A representative crystallographic reference database is the Inorganic Crystal Structure Database (ICSD) of the Fachinformationszentrum (FIZ) Karlsruhe. Other databases include the Pearson's Crystal Data (PCD) database of ASM International, the PDF-4 database of the International Centre for Diffraction Data, the Linus Pauling File of the Japan Science and Technology Corporation and the Material Phases Data System, the Crystallography Open Database, and the Nano-Crystallography Database. The data can be arranged in the standardized Crystallographic Information File (CIF) format that can be read and manipulated by a personal computer based text editor and is familiar to those of skill in the art.

In general, databases can be used to provide interfringe angle and reciprocal lattice-fringe spacing information obtained as a result of lattice-fringe fingerprinting as well as the complex structure factors of multiple crystal structures. If this information is not present explicitly, it can be calculated from other information present in the database.

Structural Fingerprinting Procedure

A process of structural fingerprinting includes steps typically intended for identifying or classifying an unknown sample based on fingerprint information. Fingerprint information can be used for identifying the crystal structure of the sample, for identifying a class of structures that a sample is part of, or, within the limit of a completely comprehensive database, for classifying a new crystal structure. Fingerprint information may be contained in the micrograph of the specimen or it may be obtained through other means. The extraction of lattice-fringe and structure factor fingerprint information from a phase-contrast image is described above. Additional information useful for structural fingerprinting may include chemical fingerprint information associated with the presence or absence of chemical elements in a sample. This information is obtainable in analytical TEMs through methods such as energy dispersive X-ray spectroscopy or electron energy loss spectroscopy. Structure factor amplitudes obtained from electron precession diffraction patterns may also be useful fingerprint information. A single type of fingerprint information may be used in the fingerprinting procedure or a combination of various types of fingerprint information may be used. Identification and classification may be performed with a computer-implemented search and match procedure using one or more databases. A crystal structure can be identified by a highest combined figure of merit out of all reference structures or by a best match in a database search combining all relevant fingerprint information.

Figure 7:
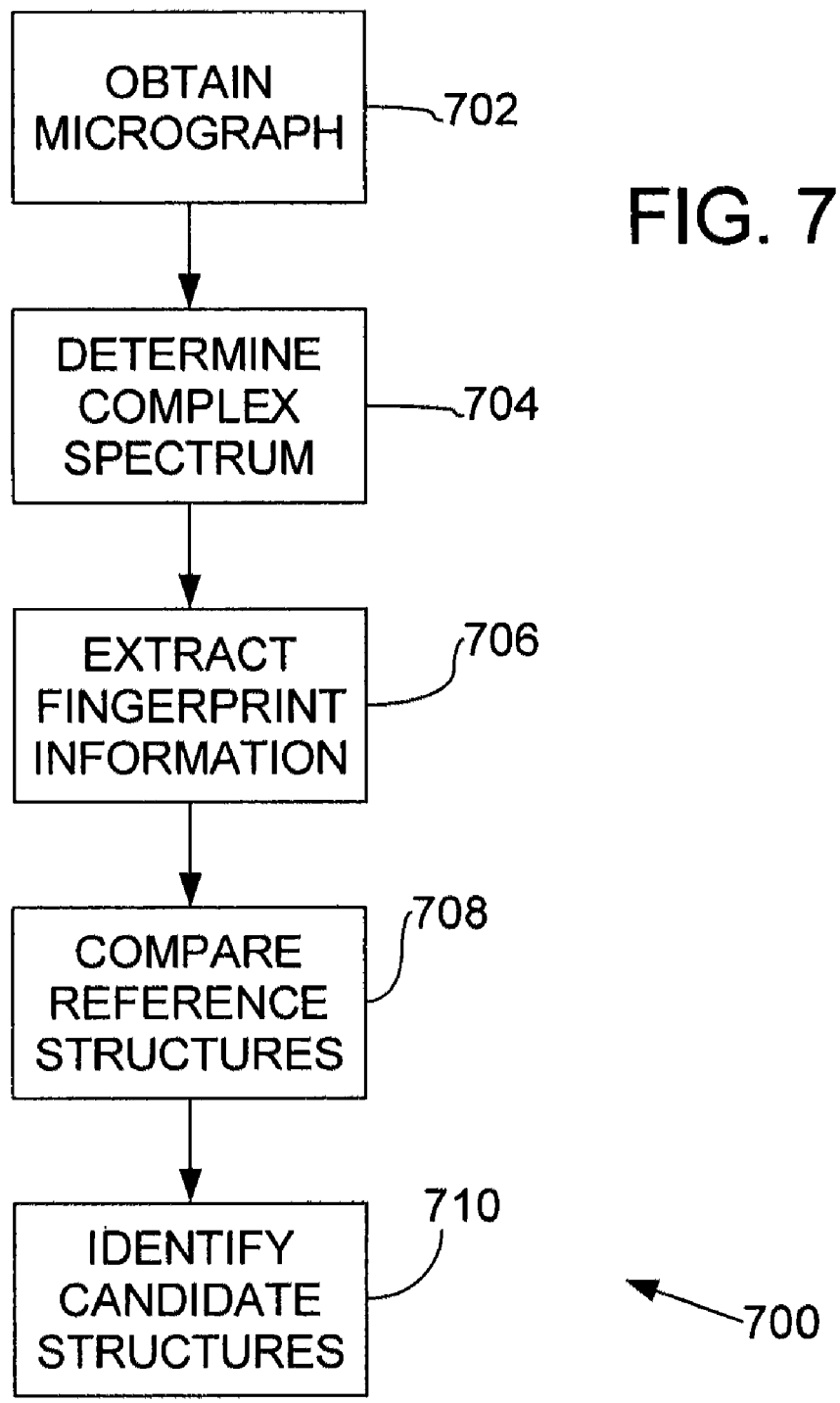
FIG. 7 is a block diagram of a representative structural fingerprinting method.

An example embodiment of a fingerprinting procedure 700 is shown in FIG. 7. In a step 702, a specimen micrograph is obtained. The micrograph can be an image taken with an electron microscope or other suitable apparatus. The image is preferably a phase-contrast image. Alternatively, the image can be an electron diffraction pattern. The image can be digitized. It can be recorded digitally or digitized after an analog recording on a suitable medium. Preferably, the imaged specimen contains nanocrystals having dimensions of a few to a few tens of nanometers but other specimens that are crystalline or partly-crystalline may be used. Preferably, any amorphous support film in the specimen is as thin as possible.

In a step 704, a crystallographically compensated complex spectrum is generated from the micrograph. The crystallographically compensated complex spectrum contains both a Fourier transform amplitude spectrum and a complementary phase portion or other representation of the phase contributions to the complex spectrum. The Fourier transform amplitude spectrum can be displayed and indexed in a similar manner to a diffraction pattern.

In a step 706, fingerprint information or other information for specimen identification is extracted from the crystallographically compensated complex spectrum. For example, lattice-fringe fingerprint information such as the reciprocal lattice vector magnitudes and the interfringe angles can be extracted. In addition, the structure factor phase and amplitude can be extracted from the complex spectrum. Structure factor amplitudes may also be obtained from a diffraction pattern or an amplitude portion of a spectrum. Fingerprint information can also include kinematically forbidden spots, and the most likely 2D symmetry group or groups. Additional fingerprint information can be obtained through other means or may be known at the time the specimen micrograph is obtained. For example, chemical fingerprint information can be acquired or it may be known that the specimen is a mineral or metal.

In a step 708, fingerprint information associated with one or more reference structures is compared with the extracted sample fingerprint information. Reference structure fingerprint information can be contained in one or more databases that are available at a single computer or workstation, or via a local area network or wide area network such as the Internet. A figure of merit can be assigned to one or more reference structures as a quantitative indicator of a structural similarity of a reference structure and the specimen. For example, a higher figure of merit of a first reference structure with respect to that of a second reference structure indicates that the first structure more closely matches the sample than the second.

In a step 710, one or more candidate structures are selected based on the comparison. If the fingerprint information used in the comparison does not permit a sufficiently exact structural identification, or no suitable candidate structures are identified, additional comparisons based on other fingerprint information can be used. Reference structures can be assigned a composite figure of merit based on each comparison, and corresponding candidate structures identified and ranked.

Typically, in the step 710, a crystal structure is identified based on the highest composite figure of merit or based on a best match for a database search combining all relevant fingerprint information. If the structure of the specimen is not identified, the specimen structure can be further determined and then added to a database as a new structure.

Figure 8:
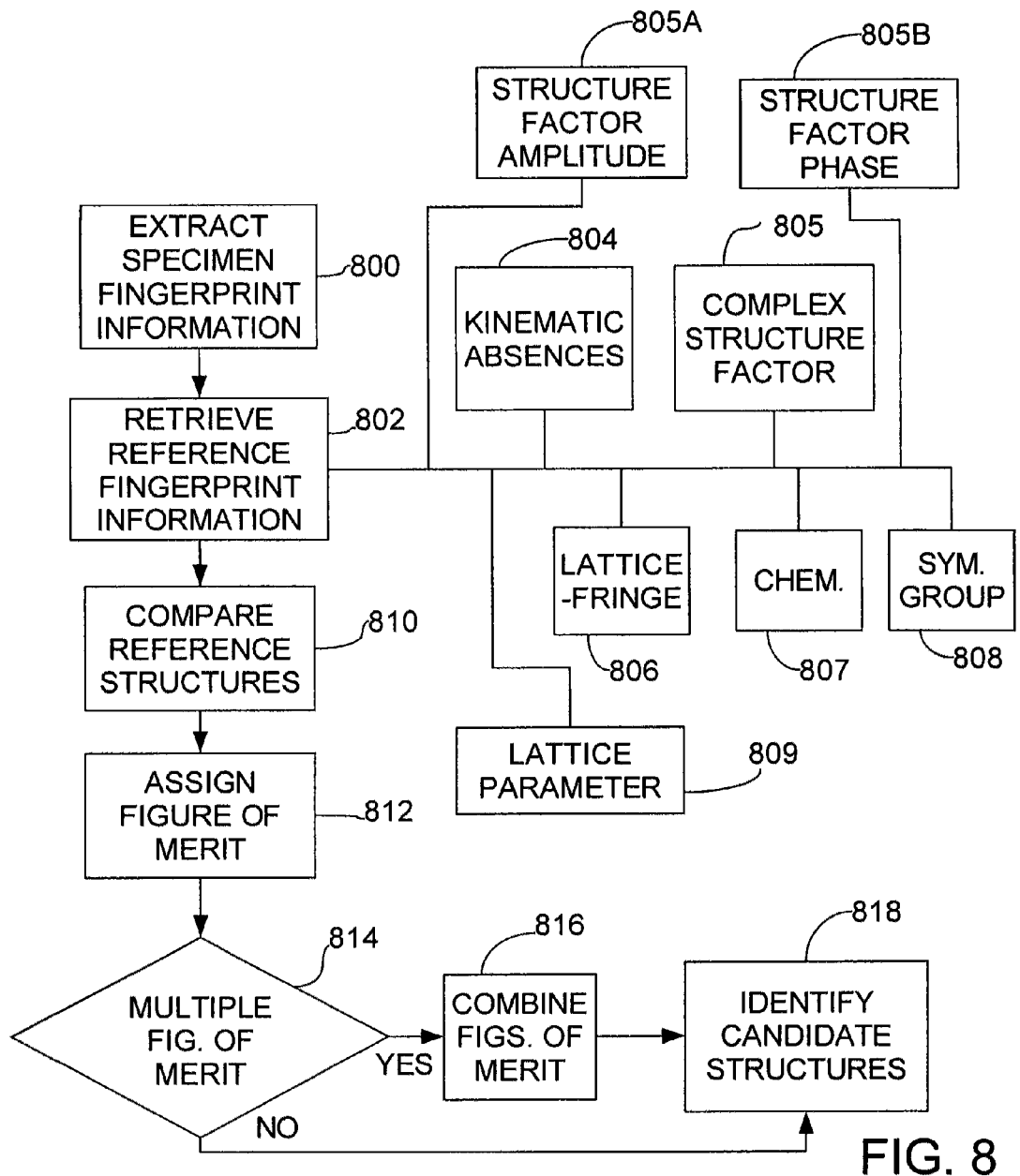
FIG. 8 is a block diagram of a representative structural fingerprinting method based on one or more types of fingerprint information.

FIG. 8 illustrates an additional representative fingerprinting method. In a step 800, sample fingerprint information is obtained, and in a step 802 reference structure fingerprint information is obtained from one or more databases such as a kinematic absence database 804, a complex structure factor database 805, a structure factor amplitude database 805A, a structure factor phase database 805B, a lattice-fringe database 806, a chemical database 807, a symmetry group database 808, or a lattice parameter database 809. Structural fingerprinting information can be stored in such databases, or can be calculated based on parameters stored in the databases. A single database can be configured for storage of all or several types of fingerprint information, and databases can be accessed via a local or wide area network such as the Internet. In a step 810, the sample and one or more reference structures are compared based on the fingerprint information, and assigned figures of merit in a step 812. If multiple figures of merit are determined to be available for one or more reference structures in a step 814, combined figures of merit are determined in a step 816. In a step 818, one or more (or no) candidate structures are identified based on the figures of merit of the reference structures. Alternatively, additional specimen information can be extracted in the step 800, and the process repeated until a satisfactory result is obtained, or a determination is made that no reference structure is likely to be suitable.

Figure 9:
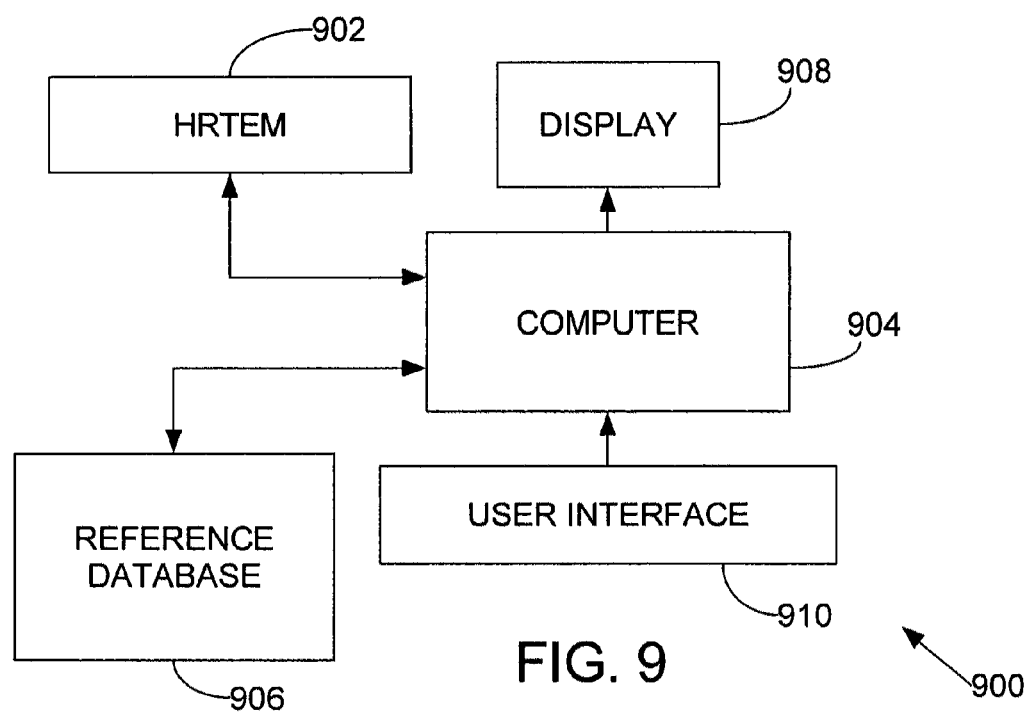
FIG. 9 is a schematic diagram of a representative apparatus for nanocrystal structure identification.

A representative structural analysis system 900 is illustrated in FIG. 9. A sample micrograph is obtained by a HRTEM 902, and a digitized micrograph of at least a portion of the sample micrograph is communicated to a computer 904 or other processor such as a workstation, laptop computer, handheld computer, or dedicated signal processing unit. The computer 904 is configured to extract fingerprint information from the micrograph and compare the sample fingerprint information with reference information obtained from a reference database 906. The computer 904 typically includes a computer-readable medium such as a hard disk or random access memory or other storage device that contains computer-executable instructions for fingerprint extraction and comparison. For example, the computer 904 can be configured to obtain a Fourier transform of the numerical representation of the micrograph, and to calculate fingerprint information or identify appropriate fingerprint information associated with one or more reference structures based on information stored in the reference database 906. Selected candidate structures can be announced by displaying suitable reference structure identifiers on a display 908. A user interface 910 is provided to permit selection of one or more types of fingerprint information for use in identifying candidate structures.

Example

Magnetite ($Fe_3O_4$)

In a representative example, fingerprinting of an individual nanocrystal from a mixture of nanocrystalline magnetite ($Fe_3O_4$), and maghemite ($\gamma$-$Fe_2O_3$) is described. High-resolution phase-contrast transmission electron micrographs of a sample that includes magnetite/maghemite are recorded at the Scherzer defocus with an HRTEM operating at 300 kV at a magnification of 240,000 and a point resolution of 0.19 nm. Such a specimen micrograph is illustrated in FIG. 2. Under these conditions, specimen reciprocal space features up to 5.26 $nm^{-1}$ are directly interpretable in the combined weak-phase object and kinematic approximations.

The micrograph is obtained as a visual image and is then digitized at 2400 pixels per inch and convolved with a Hanning window to reduce streaking in the subsequent Fourier transform calculation. The Fourier transform of the digitized micrograph is calculated and appropriate CIP is performed to generate a crystallographically compensated complex spectrum. The (uncompensated) amplitude spectrum of the image of FIG. 2 is displayed as FIG. 3. Based on the amplitude spectrum, the lengths of the reciprocal lattice vectors and their intersecting angles are derived. Lattice-fringe fingerprint information is derived from this data and is shown in FIG. 5. A theoretical lattice-fringe fingerprint plot for magnetite based on the kinematic approximation is shown in FIG. 6 in which the corresponding experimental data points from FIG. 5 are circled.

Figure 4:
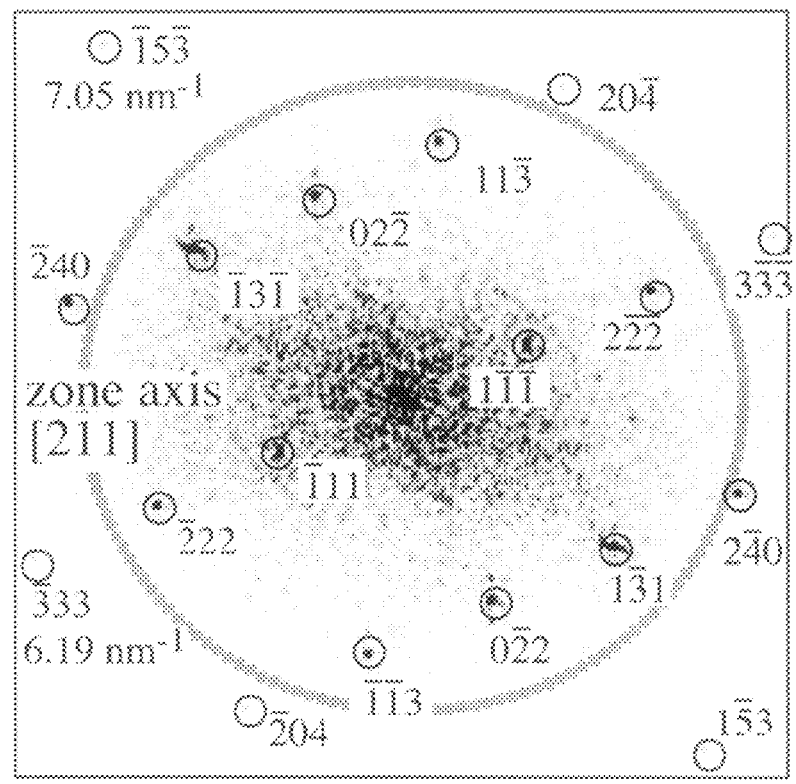
FIG. 4 is the amplitude spectrum of FIG. 3 indexed with Miller indices selected to represent the specimen crystal lattice.

The theoretical lattice-fringe fingerprint plot in FIG. 6 is calculated over a wide area network using CIFs that are part of the COD database or an inorganic subset thereof. Searches of this database can be performed with Boolean constraints based on elements absent and/or present in the experimental data and the number of elements present. After the identification of the crystal structure from a range of candidates, the Fourier transform amplitude spectrum of the specimen is indexed by 3D Miller indices as shown in FIG. 4. The Fourier transform of the HRTEM image is then scrutinized more thoroughly to ensure that the crystal structure identification is correct by comparing the structure factor information in the experimental data with the theoretically calculated values for potentially matching structures based on the phase portions of the Fourier transform of the specimen micrograph.

In view of the many possible embodiments to which the principles of the disclosed technology may be applied, it should be recognized that the illustrated embodiments are only preferred examples and should not be taken as limiting the scope of the technology. Rather, the scope of the invention is defined by the following claim and I claim as my invention all that comes within the scope and spirit of these claims.

I claim:

1. A computer-implemented method, comprising:
    with a computer, processing a transmission electron micrograph image of a specimen to determine a complex spectrum of the image so as to obtain at least partial geometrical and structure factor fingerprint information associated with the specimen;
    comparing partial specimen geometrical and structure factor fingerprint phase information with corresponding geometrical and structure factor fingerprint phase information associated with at least one candidate structure;
    selecting at least one candidate structure from a set of one or more predetermined reference structures based on a comparison of specimen lattice-fringe fingerprint phase information with lattice-fringe fingerprint phase information associated with related structural information associated with the one or more predetermined reference structures; and
    based on the comparison, communicating an assessment as to whether a specimen structure corresponds to the at least one selected candidate structure.

2. The method of claim 1, wherein obtaining the at least partial structure factor fingerprint phase information comprises determining at least a portion of a complex spectrum associated with the specimen, and wherein the specimen structure factor fingerprint phase information is based on the portion of the complex spectrum.

3. The method of claim 2, wherein the specimen structure factor fingerprint phase information is based on at least one phase of the complex spectrum.

4. The method of claim 3, wherein the complex spectrum is a crystallographically compensated complex spectrum.

5. The method of claim 3, further comprising selecting the at least one candidate structure from a set of one or more predetermined reference structures based on a comparison of specimen chemical fingerprint information with chemical fingerprint information associated with the one or more predetermined reference structures.

6. The method of claim 3, further comprising obtaining lattice-fringe fingerprint information for at least one reference structure from at least one database.

7. The method of claim 6, further comprising adding lattice-fringe fingerprint information for the specimen to the at least one database.

8. The method of claim 3, wherein assessing whether a specimen structure corresponds to at least one of the candidate structures includes assigning a figure of merit to the at least one candidate structure.

9. The method of claim 1, wherein the geometrical fingerprint information associated with the specimen is obtained based on an electron diffraction pattern.

10. The method of claim 9, wherein the electron diffraction pattern is an electron precession based diffraction pattern.

11. One or more computer-readable storage media, the computer-readable storage media not being a propagating signal comprising computer-executable instructions for performing the method of claim 1.

12. A method, comprising:

with a computer, obtaining at least partial geometrical and structure factor fingerprint information associated with a specimen based on lattice-fringe fingerprint information, wherein the lattice-fringe fingerprint information is based on a Fourier transform of a phase contrast image of the specimen;

comparing partial specimen geometrical and structure factor fingerprint amplitude information with corresponding geometrical and structure factor fingerprint amplitude information associated with at least one candidate structure; and based on the comparison, communicating an assessment as to whether a specimen structure corresponds to the at least one candidate structure.

13. The method of claim 12, further comprising obtaining at least a portion of the specimen geometrical structure factor fingerprint amplitude information by precession electron diffraction.

14. The method of claim 12, further comprising obtaining a phase contrast image of the specimen, and obtaining the lattice-fringe fingerprint information from the phase contrast image.

* * * * *